US012426836B2

(12) United States Patent
Hynynen

(10) Patent No.: US 12,426,836 B2
(45) Date of Patent: Sep. 30, 2025

(54) PATIENT-SPECIFIC HEADSET FOR DIAGNOSTIC AND THERAPEUTIC TRANSCRANIAL PROCEDURES

(71) Applicant: SUNNYBROOK RESEARCH INSTITUTE, Toronto (CA)

(72) Inventor: Kullervo Henrik Hynynen, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 0 days.

(21) Appl. No.: 18/239,288

(22) Filed: Aug. 29, 2023

(65) Prior Publication Data
US 2023/0397881 A1 Dec. 14, 2023

Related U.S. Application Data

(62) Division of application No. 16/078,903, filed as application No. PCT/CA2017/050230 on Feb. 23, 2017, now Pat. No. 11,771,370.
(Continued)

(51) Int. Cl.
A61B 5/00 (2006.01)
A61B 5/055 (2006.01)
(Continued)

(52) U.S. Cl.
CPC ............ A61B 5/6803 (2013.01); A61B 5/055 (2013.01); A61B 5/4064 (2013.01); A61B 5/6814 (2013.01); A61B 5/6835 (2013.01); A61B 6/03 (2013.01); A61B 8/0808 (2013.01); A61B 8/42 (2013.01); A61B 8/4281 (2013.01);
(Continued)

(58) Field of Classification Search
CPC ........ A61B 2560/0425; A61B 2562/12; A61B 2562/16; A61B 2576/026; A61B 5/055; A61B 5/4064; A61B 5/4848; A61B 5/6803; A61B 5/6814; A61B 5/6835; A61B 6/03; A61B 8/0808; A61B 8/42; A61B 8/4281; A61B 8/4488; A61B 90/14; A61N 2007/0078; A61N 7/00; A61N 7/02; G16H 30/40
See application file for complete search history.

(56) References Cited

U.S. PATENT DOCUMENTS 8,086,336 B2* 12/2011 Christensen .......... A61F 2/2875
700/118
2004/0210134 A1* 10/2004 Hynynen ............... A61B 8/485
601/2
(Continued)

Primary Examiner — Michael T Rozanski
(74) Attorney, Agent, or Firm — Stephen Leonard; Aird & McBurney LP

(57) ABSTRACT

Systems, methods and devices are provided for performing diagnostic or therapeutic transcranial procedures using a patient-specific transcranial headset. The patient-specific headset may include a patient-specific frame that is fabricated, according to volumetric image data, to conform to an anatomical curvature of a portion of a patient's head. The patient-specific frame is configured to support a plurality of transducers in pre-selected positions and orientations, which may be spatially registered to the volumetric image data. This spatial registration may be employed to control at least a portion of the transducers to focus energy at a preselected tissue region.

20 Claims, 6 Drawing Sheets

Related U.S. Application Data

(60) Provisional application No. 62/298,873, filed on Feb. 23, 2016.

(51) Int. Cl.
  *A61B 6/03* (2006.01)
  *A61B 8/00* (2006.01)
  *A61B 8/08* (2006.01)
  *A61B 90/14* (2016.01)
  *A61N 7/00* (2006.01)
  *A61N 7/02* (2006.01)

(52) U.S. Cl.
  CPC ............ *A61B 8/4488* (2013.01); *A61B 90/14* (2016.02); *A61N 7/00* (2013.01); *A61N 7/02* (2013.01); *A61B 5/4848* (2013.01); *A61B 2560/0425* (2013.01); *A61B 2562/12* (2013.01); *A61B 2562/16* (2013.01); *A61B 2576/026* (2013.01); *A61N 2007/0078* (2013.01)

(56) References Cited

U.S. PATENT DOCUMENTS

| | | | |
|---|---|---|---|
| 2006/0241529 A1* | 10/2006 | Hynynen | A61B 8/0816 601/2 |
| 2012/0046716 A1 | 2/2012 | Dougal | |
| 2015/0099963 A1* | 4/2015 | Navarro de Lara | A61B 5/055 324/322 |
| 2015/0115162 A1* | 4/2015 | Tashima | A61B 6/037 250/363.03 |

\* cited by examiner

PATIENT-SPECIFIC HEADSET FOR DIAGNOSTIC AND THERAPEUTIC TRANSCRANIAL PROCEDURES

CROSS-REFERENCE TO RELATED APPLICATION

This application is a divisional application and claims priority to U.S. patent application Ser. No. 16/078,903, filed Aug. 22, 2018. U.S. patent application Ser. No. 16/078,903 is a national stage entry of PCT/CA2017/050230, with international filing date Feb. 23, 2017. PCT/CA2017/050230 claims priority to U.S. Provisional Application No. 62/298,873, titled PATIENT-SPECIFIC HEADSET FOR DIAGNOSTIC AND THERAPEUTIC TRANSCRANIAL PROCEDURES" and filed on Feb. 23, 2016, the entire contents of which is incorporated herein by reference.

BACKGROUND

The present disclosure relates to transcranial diagnostic and therapeutic procedures.
The application of focused ultrasound to the brain through the intact skull has a long history leading up to the clinical implementations of the present day. Since the first successful ablation of animal brain tissue transcranially using a single transducer in 1980, to the present day multi-center clinical trials of Magnetic Resonance (MR)-guided focused ultrasound for the treatment of essential tremor using hemispherical phased arrays consisting of more than one thousand elements, new phased array designs have been conceptualized to overcome previous challenges, such as skull aberration correction, standing wave reduction, skull heating, and dual-frequency blood-brain barrier disruption.

SUMMARY

Systems, methods and devices are provided for performing diagnostic or therapeutic transcranial procedures using a patient-specific transcranial headset. The patient-specific headset may include a patient-specific frame that is fabricated, according to volumetric image data, to conform to an anatomical curvature of a portion of a patient's head. The patient-specific frame is configured to support a plurality of transducers in pre-selected positions and orientations, which may be spatially registered to the volumetric image data. This spatial registration may be employed to control at least a portion of the transducers to focus energy at a pre-selected tissue region.

Accordingly, in a first aspect, there is provided a system for performing diagnostic or therapeutic transcranial procedures, the system comprising:
a patient-specific transcranial headset comprising:
  a patient-specific frame configured to conform to an anatomical curvature of a portion of a patient's head, said patient-specific frame having been fabricated based on volumetric image data associated with the patient;
  a plurality of transducers supported by said patient-specific frame, wherein said plurality of transducers are supported in pre-selected positions and orientations relative to said patient-specific frame; and
control and processing hardware operably connected to said plurality of transducers, wherein said control and processing hardware is configured to:
  obtain transducer registration data spatially registering the pre-selected positions and orientations of said plurality of transducers with the volumetric image data; and
  control at least a portion of said plurality of transducers to focus energy at a pre-selected tissue region.

In another aspect, there is provided a method of fabricating a transcranial headset for diagnostic or therapeutic procedures, the method comprising:
  obtaining, from volumetric image data of a patient's head, surface data characterizing an anatomical curvature of a portion of the patient's head;
  employing the surface data to generate a digital model of a patient-specific frame, such that the patient-specific frame conforms to the anatomical curvature of the portion of the patient's head;
  modifying the digital model such that the patient-specific frame comprises a plurality of transducer attachment interfaces for receiving and supporting a plurality of transducers in pre-selected positions and orientations relative to the patient's head;
  fabricating the patient-specific frame according to the digital model;
  securing the plurality of transducers to the transducer attachment interfaces; and
  generating transducer registration data characterizing the positions and orientations of the plurality of transducers relative to the volumetric image data.

In another aspect, there is provided a kit for performing diagnostic or therapeutic transcranial procedures, the kit comprising:
a patient-specific transcranial headset comprising:
  a patient-specific frame configured to conform to an anatomical curvature of a portion of a patient's head, said patient-specific frame having been fabricated based on volumetric image data associated with the patient;
  a plurality of transducers supported by said patient-specific frame, wherein said plurality of transducers are supported in pre-selected positions and orientations relative to said patient-specific frame; and
transducer registration data spatially registering the pre-selected positions and orientations of said plurality of transducers with the volumetric image data.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
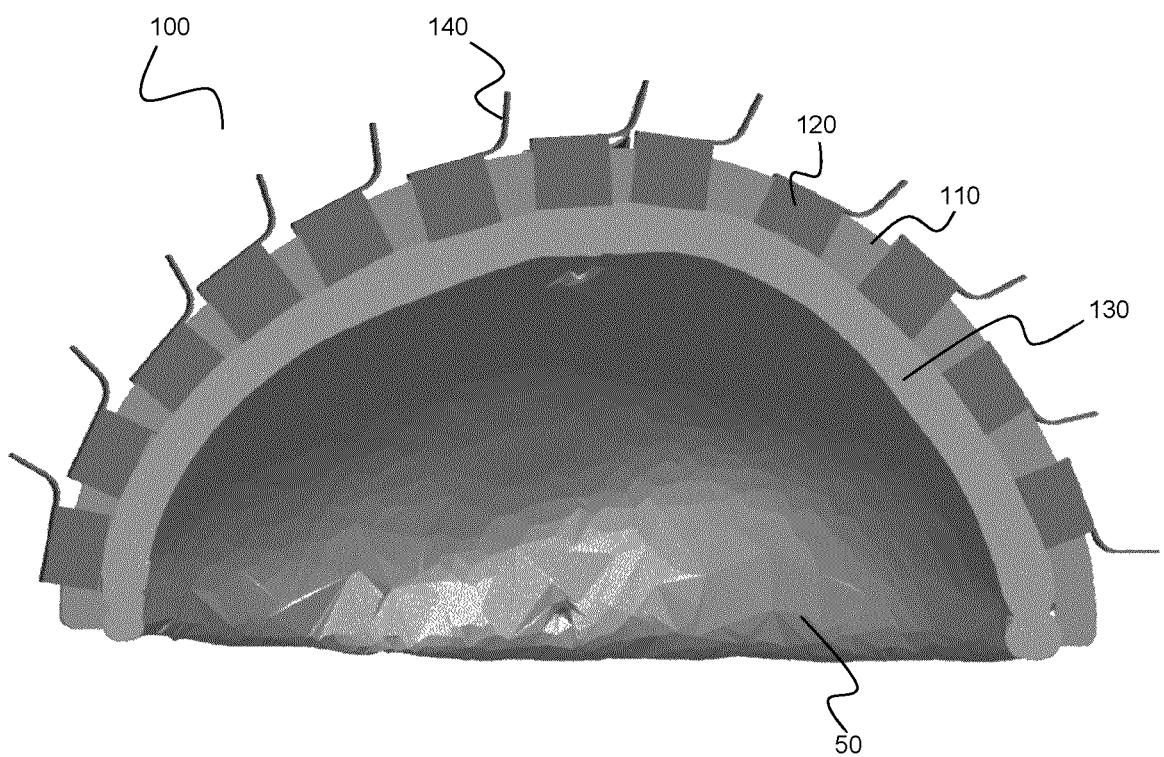
FIG. 1 shows a cross-sectional illustration of an example patient-specific headset for performing transcranial diagnostic and/or therapeutic procedures.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "pre-operative" refers to an action, process, method, event or step that occurs or is carried out prior to a medical procedure. Pre-operative, as defined herein, is not limited to surgical procedures, and may refer to other types of medical procedures, such as diagnostic and therapeutic procedures.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Referring now to FIG. 1, a patient-specific headset 100 for performing transcranial diagnostic or therapeutic procedures is shown worn on the head 50 of a patient. The patient-specific headset 100, which includes a patient-specific frame (support structure) 110 that supports a plurality of transducers 120, conforms to the anatomical contour of at least a portion of the patient's head. The patient-specific frame 110, which is shown in cross-section in FIG. 1, mechanically supports transducers 120 in pre-selected positions and orientations. The transducers 120 may be used to transmit and/or receive energy for brain diagnostic or therapeutic purposes or for localization of the skull surface.

The patient-specific frame 110 includes a plurality of attachment interfaces for receiving and supporting the transducers 120. In the example embodiment shown in FIG. 1, the attachment interfaces are provided as apertures (recesses) into which the transducers 120 are placed. The transducers 120 may be affixed to the patient-specific frame 110 according to a wide variety of different means, such as, but not limited to, with an attachment mechanism (e.g. via fasteners that extend into the patient-specific frame 110, optionally into pre-formed holes), or an adhesive such as a glue. In the example implementation shown in FIG. 1, the transducers 120 are remotely interfaced with electronics through wires or through a flexible printed circuit board 140. The transducers 120 may be removably attachable to the patient-specific frame 110.

As shown in FIG. 1, the patient-specific headset may also include a coupling layer 130 that is provided adjacent to an inner surface of the patient-specific frame. The outer surface of the coupling layer 130 contacts distal surfaces of the transducers 120, and the inner surface of the coupling layer contacts the patient's head 50, thereby facilitating coupling of energy between the transducers in the patient-specific frame and the patient's head. The inclusion of the coupling layer 130, and the composition and/or geometry of the coupling layer, may be dependent on the type of transducers 120. For example, if the transducers 120 are ultrasound transducers, the coupling layer 130 may be an acoustic coupling layer that facilitates propagation of acoustic waves and reduces reflections at interfaces. In one example implementation, the coupling layer 130 includes an elastic membrane that retains a liquid layer between the transducer surfaces and the elastic membrane, such that coupling to the skin is achieved.

Although FIG. 1 shows an example embodiment in which the transducers are ultrasound transducers, it will be understood that the transducers may be any transducers capable of emitting or receiving energy. Non-limiting examples of different types of transducers include ultrasound transducers configured to emit and/or receive ultrasound energy, magnetic resonance coils (radio-frequency coils) and optical transducers such as lasers, light emitting diodes, and optical fibers coupled to sources and/or detectors. The transducers need not all be of the same type, and a first portion of the transducers may be selected to emit and/or detect a first type of energy (e.g. ultrasound), and another portion of the transducers may be selected to emit and/or detect a second type of energy (e.g. optical or electromagnetic waves).

In one example implementation, a first subset of the transducers may be ultrasound transducers, and a second subset of the transducers may be optical transducers (e.g. optical fibers in optical communication with a source and/or detector), such that the patient-specific headset is capable of performing photoacoustic imaging.

In another example implementation, a first subset of the transducers may be ultrasound transducers, and a second subset of the transducers may be MRI coils, such that the system is suitable for performing simultaneous ultrasound and MR imaging or sonications while using MR imaging.

In another example implementation, a first subset of the transducers may be MRI coils, and a second subset of the transducers may be positron emission detector (PET), such that the system is suitable for performing both MR and PET imaging.

In another example implementation, a first subset of the transducers may be MRI coils, and wherein a second subset of the transducers may be positron emission detector (PET), and third subset of the transducers may be ultrasound transducer, such that said system is suitable for performing both MR and PET imaging while delivering ultrasound therapy or imaging.

In some example embodiments, at least a portion of the transducers are may be transducer elements for forming a phased array (i.e. the transducers may be phased-array transducers). Such phased-array transducers may be spatially arranged on the patient-specific headset to provide a full phased array, or a sparse phased array.

In some example embodiments, the phased-array transducers may be provided as a plurality of sub-arrays, where each sub-array is mechanically supported as a separate transducer module, such that each transducer module is mechanically supported on the patient-specific frame 110 by a respective attachment interface. For example, referring to FIG. 1, each transducer 120 may be a transducer module housing a sub-array of transducers, such that the sub-arrays, spatially distributed on the patient-specific headset 100, separately form distinct phased arrays, or collectively form a composite phased-array. The transducer modules, and their respective attachment interfaces, may have unique shapes (i.e. they may be respectively keyed), such that a given transducer module fits uniquely with its respective attachment interface. If the phased array is formed by a set of transducer modules housing respective sub-arrays, the transducer modules may be spatially distributed on the patient-specific frame to reduce or minimize the formation of grating lobes.

Figure 2:
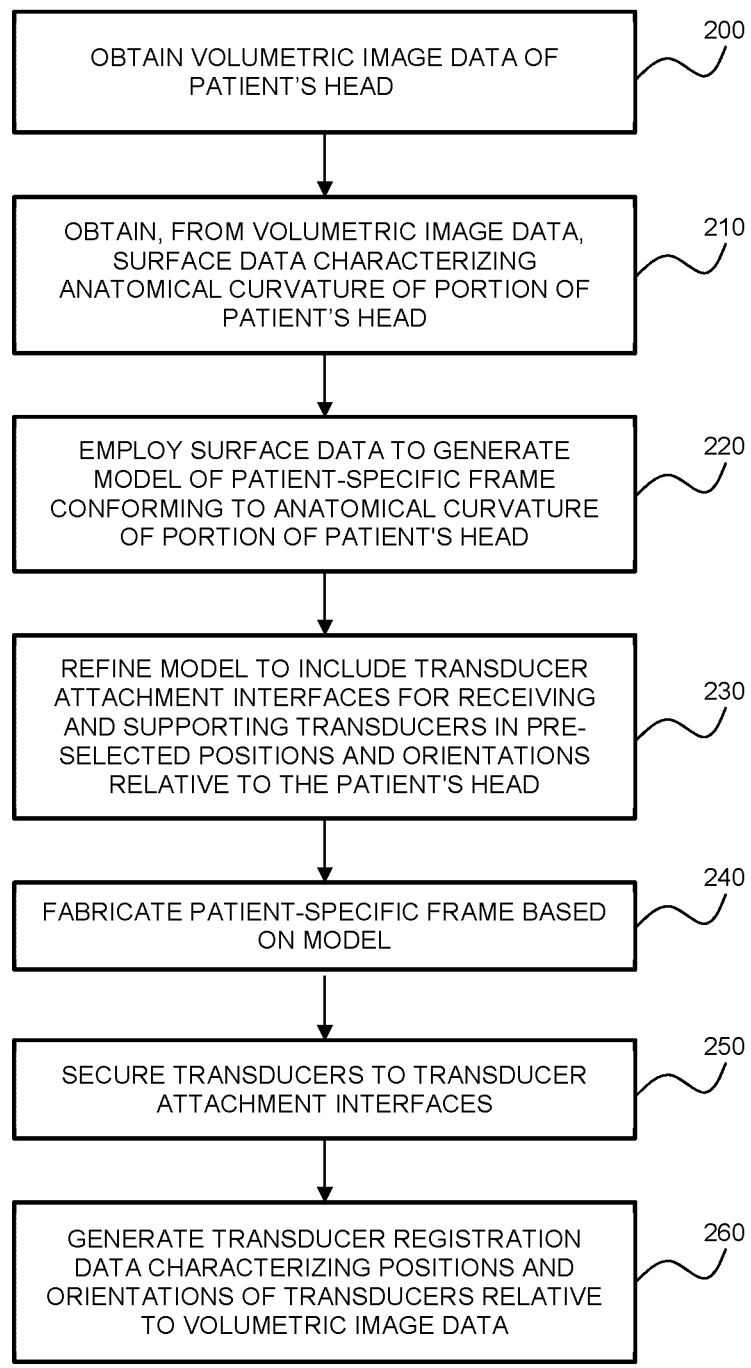
FIG. 2 is a flow chart illustrating an example method of fabricating a patient-specific headset.

As noted above, the patient-specific frame conforms to the anatomical contour of at least a portion of the patient's head. Such a conformal frame may be fabricated based on volumetric image data of the patient's head. FIG. 2 illustrates an example method for fabricating a patient-specific frame based on volumetric image data associated with the patient. In steps 200 and 210, volumetric image data of a patient's head is obtained and processed to provide surface data characterizing an anatomical curvature (e.g. skin or bone surface) of a portion of the patient's head. The volumetric data may be obtained, for example, by performing imaging using an imaging modality such as, but not limited to, magnetic resonance (MR) imaging and computed tomography (CT) imaging. The volumetric image data may be obtained based on a previously performed imaging procedure.

The volumetric image data may be processed and segmented to obtain surface data characterizing the surface of a portion of the patient's skull. Such surface segmentation may be performed, for example, using imaging processing software such as the Mimics™ software platform (Materialise, Belgium). Such software enables the creation of a 3D model (the surface data) of the surface of a portion of the patient's head. The model may be created using known techniques, such as using the steps of thresholding, region growing and manual editing. Automatic thresholding may be performed to achieve a first approximation of the bony surfaces of the skull, followed by manual editing to obtain a refined model. Haptic modeling, for example using a modeling software platform such as the PHANTOM™ Desktop Haptic Device, may be used to further refine the model. Additional example methods of image processing and segmentation of volumetric image data are disclosed in U.S. Pat. No. 8,086,336.

Subsequently, as shown in step 220, the surface data is used to produce a digital model of the patient-specific frame. For example, a suitable software platform (such as the software package Surfacer™) may be employed to generate a model based on a point cloud of surface data points. As shown at step 230, the model is then modified or refined (e.g. updated) to include a plurality of transducer attachment interfaces for receiving and supporting a plurality of transducers in pre-selected positions and orientations relative to the patient's head, and for supporting the transducers such that energy is coupled transcranially.

The positions and orientations of the transducer attachment interfaces may be selected, for example, to form one or more phased arrays of transducers. In embodiments in which sub-arrays are formed by a set of transducer modules housing respective sub-arrays, the transducer modules may be spatially distributed on the patient-specific frame to reduce or minimize the formation of grating lobes.

The digital model may be further refined to include one or more additional features, such as, but not limited to, an attachment interface for the attachment of one or more fiducial markers, an aperture to permit surgical access to a selected region of the patient's head when the patient-specific frame is worn, markers for identifying reference directions, and one or more positioning features such as external handles.

The digital model, updated to include the transducer attachment interfaces, is then employed to fabricate the patient-specific frame, as shown at step 240. For example, the patient-specific frame may be fabricated from the model using 3D printing. In another example, the model may be employed to produce a mold suitable for forming the patient-specific frame, and the mold may be subsequently employed to fabricate the patient-specific frame.

After having fabricated the patient-specific frame, the transducers (or transducer assemblies or modules) are secured (attached, adhered, etc.) to the respective transducer attachment interfaces of the patient-specific frame, as shown at step 250.

In order to employ the patient-specific headset for performing diagnostic or therapeutic procedures based on preoperative volumetric image data, a relationship may be established between the positions and orientations of the transducers and the volumetric image data (i.e. so that both can be represented within a common reference frame). Accordingly, in step 260, the known positions and orientations of the transducers (as prescribed in the digital model) are spatially registered relative to the volumetric image data, thereby generating transducer registration data characterizing the positions and orientations of the transducers relative to the volumetric image data. For example, such transducer registration data may include the spatial coordinates of the transducers, and vectors identifying their respective orientations, in the reference frame of the volumetric data. In another example implementation, the transducer registration data may include a coordinate transformation for transforming the positions and orientations of the transducers from a first reference frame to the reference frame of the volumetric image data. The transducer registration data enables the determination of the positions and orientations of the transducers relative to the volumetric image data, enabling, for example, the determination of suitable beamforming parameters to pulse one or more phased arrays (e.g. sub-arrays) of transducers to focus an energy beam at a specific location or region within the patient's head.

In some example embodiments, a subset of transducers may be configured to emit an energy beam toward the skull of the patient and to detect energy that is reflected from the skull in order to facilitate the detection, for each transducer in the subset of transducers, of a local spatial offset of the skull of the patient relative to the patient-specific frame. The detected spatial offsets may then be employed to correct a spatial registration of the transducers relative to the patient anatomy (e.g. the skull and/or one or more internal tissue regions of interest) or to perform corrections based on the detected signals, for example, as disclosed in U.S. Pat. No. 6,612,988. For example, the subset of transducers may be ultrasound transducers, or, for example, optical fibers operably connected to an optical coherence tomography system.

In another embodiment, the registration between the headset and the head and brain can be achieved by performing imaging (for example MRI, CT, thomosynthesis, or x-ray) with the headset placed on the subjects head, allowing the transducer locations to be determined from the imaging visible fiducial markers in the headset.

Figure 3:
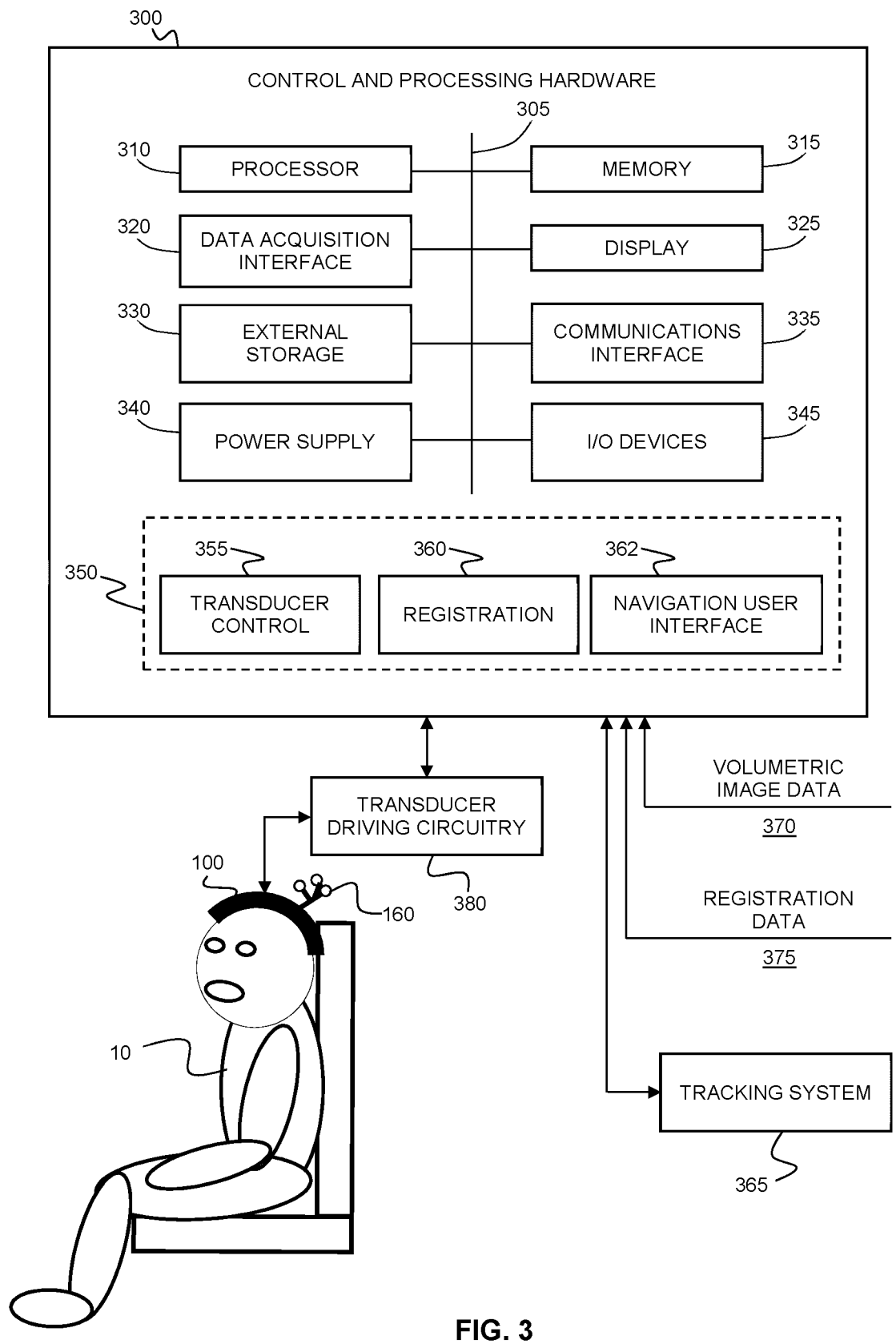
FIG. 3 shows a system for performing transcranial diagnostic and/or therapeutic procedures.

FIG. 3 provides a block diagram illustrating an example implementation of a system for performing diagnostic or therapeutic transcranial procedures. Control and processing hardware 300 is operably connected to the patient-specific transcranial headset 100, optionally via transducer driver electronics/circuitry 380.

The control and processing hardware 300, which includes one or more processors 310 (for example, a CPU/microprocessor), bus 305, memory 315, which may include random access memory (RAM) and/or read only memory (ROM), a data acquisition interface 320, a display 325, external storage 330, one more communications interfaces 335, a power supply 340, and one or more input/output devices and/or interfaces 345 (e.g. a speaker, a user input device, such as a keyboard, a keypad, a mouse, a position tracked stylus, a position tracked probe, a foot switch, and/or a microphone for capturing speech commands).

Volumetric image data 370 and transducer registration data 375 may be stored on an external database or stored in memory 315 or storage 330 of control and processing hardware 300.

The tracking system 365 may optionally be employed to track the position and orientation of the patient, via detection of one or more fiducial markers 160 attached to the patient-specific headset 100, and optionally one or more medical instruments or devices also having fiducial markers attached thereto. For example, passive or active signals emitted from the fiducial markers may be detected by a stereographic tracking system employing two tracking cameras. The transducer driving electronics/circuitry 380 may include, for example, but is not limited to, Tx/Rx switches, transmit and/or receive beamformers.

The control and processing hardware 300 may be programmed with programs, subroutines, applications or modules 350, which include executable instructions, which when executed by the one or more processors 310, causes the system to perform one or more methods described in the present disclosure. Such instructions may be stored, for example, in memory 315 and/or other storage.

In the example embodiment shown, the transducer control module 355 includes executable instructions for controlling the transducers of the patient-specific transcranial headset 100 to deliver energy to a target location or region of interest, based on the registration of the transducer positions and orientations with the volumetric image data as per the transducer registration data 375. For example, the patient-specific headset 100 may support a plurality of phased-array transducers, and transducer control module 355 may control the beamforming applied (on transmit and/or receive) to deliver, based on the known positions and orientations of the phased array transducers relative to the volumetric image data, one or more focused energy beams to a region of interest. The region of interest may be specified intraoperatively by a user (e.g. via a user interface controlled by control and processing hardware 300) or according to a pre-established surgical plan.

The registration module 360 may optionally be employed for registering volumetric image data 370 to an intraoperative reference frame associated with tracking system 365. The optional guidance user interface module 362 includes executable instructions for displaying a user interface showing spatially registered volumetric images for image-guided procedures. The registration module 360 may also intraoperatively receive spatial correction information based on a detected spatial offset between the patient-specific frame and the patient's head (which, as described above, may be provided by a subset of distance-sensing transducers) and employ this spatial correction information to dynamically adjust (e.g. correct) the registration between the transducers and the volumetric image data.

Although only one of each component is illustrated in FIG. 3, any number of each component can be included in the control and processing hardware 300. For example, a computer typically contains a number of different data storage media. Furthermore, although bus 305 is depicted as a single connection between all of the components, it will be appreciated that the bus 305 may represent one or more circuits, devices or communication channels which link two or more of the components. For example, in personal computers, bus 305 often includes or is a motherboard. Control and processing hardware 300 may include many more or less components than those shown.

The control and processing hardware 300 may be implemented as one or more physical devices that are coupled to processor 310 through one of more communications channels or interfaces. For example, control and processing hardware 300 can be implemented using application specific integrated circuits (ASICs). Alternatively, control and processing hardware 300 can be implemented as a combination of hardware and software, where the software is loaded into the processor from the memory or over a network connection.

Some aspects of the present disclosure can be embodied, at least in part, in software, which, when executed on a computing system, transforms a computing system into a specialty-purpose computing system that is capable of performing the methods disclosed herein. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

The patient-specific headset and associated transducer registration data may be employed for a wide variety of transcranial procedures, including, but not limited to, neuromodulation, neurostimulation, neuroimaging, neuromonitoring, focused-ultrasound transcranial ablation, mild heating (hyperthermia), neuromodulation, neurostimulation, mechanical excitation of the brain for diagnostic or therapeutic purposes, manipulation, control, excitation or sensing of gas bubbles, liquid droplets, solid particles, cells, nanoparticles, quantum dots or electronic circuits or devices, focused-ultrasound transcranial excitation or sensing of brain implants, devices, electronic circuits or sensors and transcranial procedures involving the use of focused ultrasound to disruption and opening of the blood-brain barrier for delivery of therapeutic or diagnostic agents, cells, particles, droplets, bubbles, electronic devices, transmitters, sensors or other foreign material for diagnostic purposes.

It will be understood that although the present disclosure includes many example embodiments pertaining to a patient-specific headset that is to be worn on the patient's head, the systems, devices and method disclosed herein may be adapted to provide a patient-specific apparatus for performing diagnostic or therapeutic procedures on other parts or portions of the body. The patient-specific frame may be fabricated according to volumetric image data of other body regions or body portions. For example, a patient-specific frame may be fabricated, based on volumetric image data of a patient's knee, such that the patient-specific frame conforms to the contour of the patient's knee, for performing a diagnostic or therapeutic procedure on the knee using the transducer supported by the patient-specific frame. Similarly, a patient-specific frame may be fabricated, based on volumetric image data of a patient's spine, such that the patient-specific frame conforms to the contour of the patient's spine, for performing a diagnostic or therapeutic procedure on the spine using the transducer supported by the patient-specific frame.

EXAMPLES

The following examples are presented to enable those skilled in the art to understand and to practice embodiments of the present disclosure. They should not be considered as a limitation on the scope of the disclosure, but merely as being illustrative and representative thereof.

Figure 4:
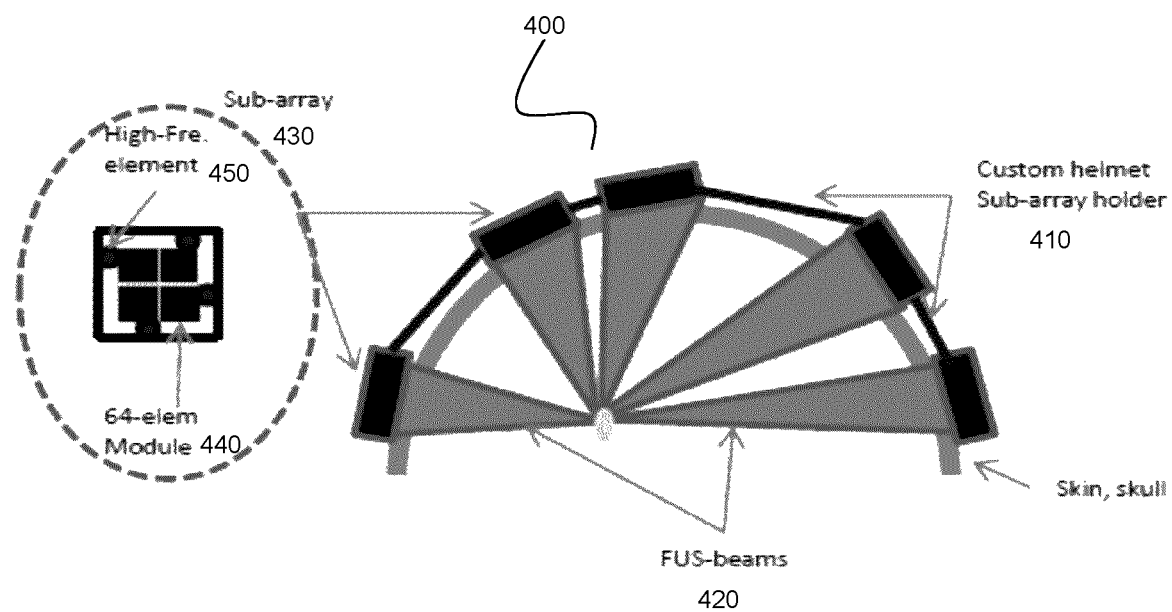
FIG. 4 shows an example implementation of a patient-specific headset that includes a plurality of ultrasound modules, each module supporting a sub-array of phased-array ultrasound transducers.

Referring now to FIG. 4, an example patient-specific headset 400 is shown, where the patient specific frame 410 (sub-array holder) supports a plurality of focused ultrasound phased array transducers. This example system may be employed, for example, for neuromodulation experiments or treatments in humans or large animals.

Figure 5A:
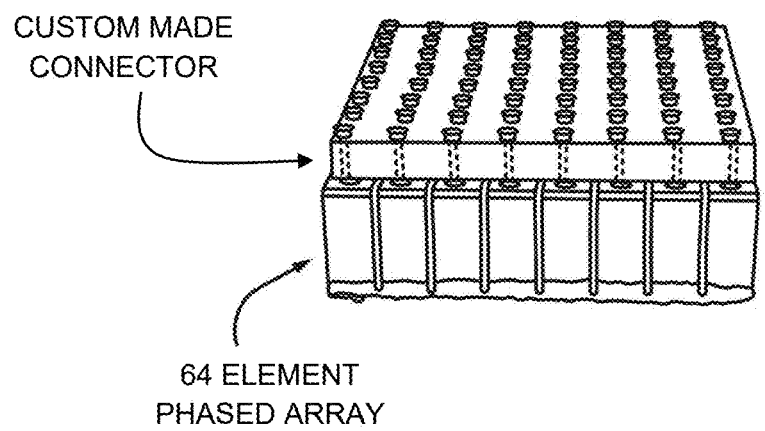
FIG. 5A shows a photograph of an example ultrasound transducer module.
Figure 5B:
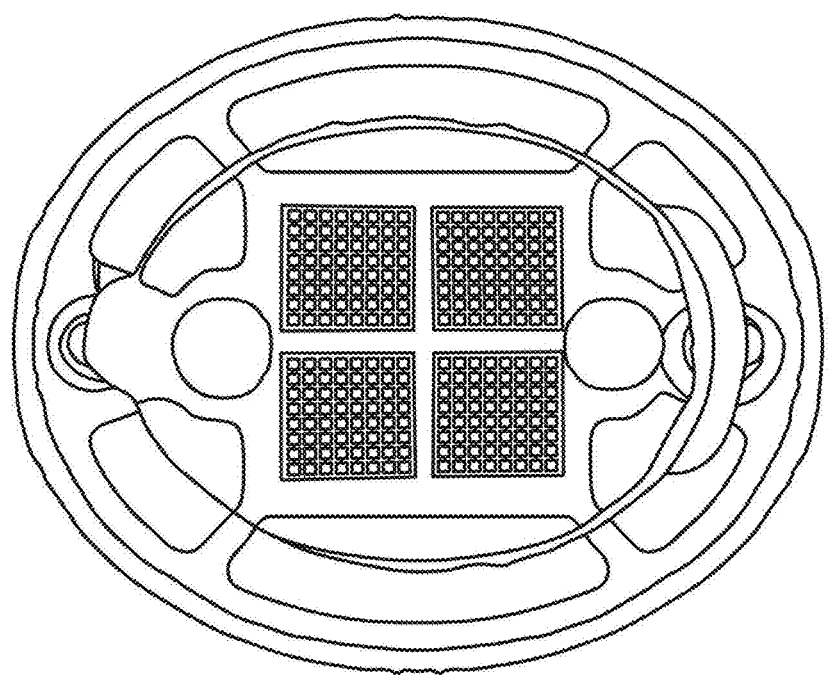
FIG. 5B shows a photograph of an example patient-specific headset, showing a plurality of ultrasound modules, each module supporting a sub-array of phased-array ultrasound transducers.
Figure 5C:
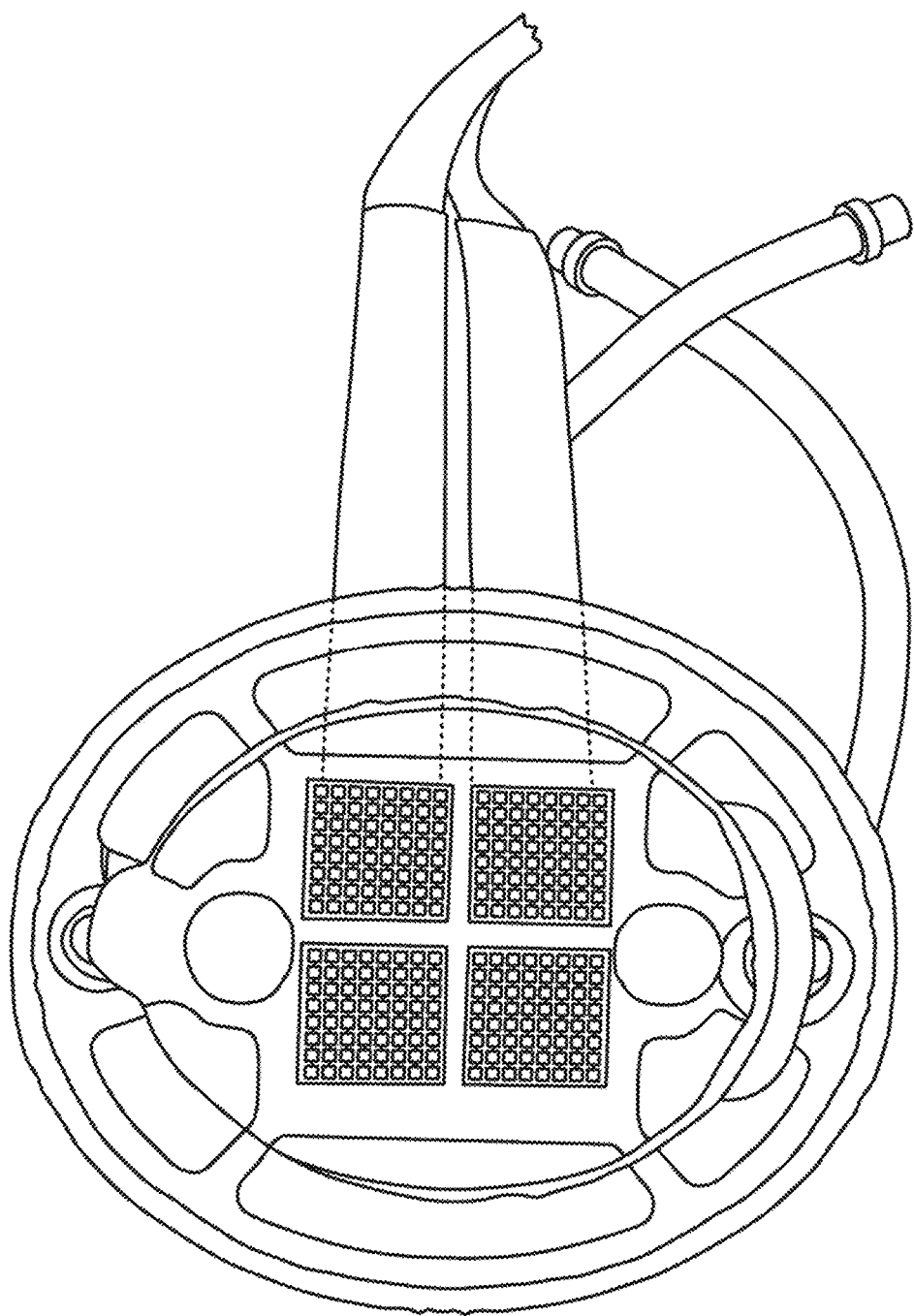
FIG. 5C shows a photograph of an example patient-specific headset, showing a plurality of ultrasound modules connected to external driving circuiting via flexible cables.

As shown in FIG. 4, ultrasound beams 420 are generated by multiple transducer sub-array modules 430, where each transducer sub-array module includes, in one example implementation, a set of 64 transducer elements spaced at the center-to-center distance of half-wavelength, making complete electronic beam steering possible. For example, at an ultrasound frequency of 500 kHz, the module size of the aforementioned example implementation would be approximately 8.5 mm×8.5 mm, but will scale inversely with frequency. Larger center-to-center spacing could be used by limiting the steering range, accepting some grating lobes, or by making the array surface curved such that it and only steering the array focus to a limited volume of tissue. Each of the modules may be connected to a 64-channel RF-driving board via a flex circuit. A photograph of an example of such a sub-array module is shown in FIG. 5A. FIGS. 5B and 5C shows an image of a plurality of sub-modules assembled and supported on a patient-specific frame.

In one example implementation, the aforementioned modules may be provided as sub-modules 440 that form a sub-array module 430 connected to a rigid base that will support and hold the module in place. Each sub-array module 430 may also house one or more (e.g. four) PVDF-wideband receivers 450 to detect reflections from the skull surfaces and scattering from the brain tissue. The location and number of these modules may be selected, on a per-patient basis, based on computer simulations, such that they all form a sparse (e.g. optimal) array where the distances between the modules have suitable (e.g. maximal) variability to prevent grating lobe formation.

As noted above, the computer simulations employ volumetric image data (e.g. MRI or CT-scans) of the subject's head to obtain a model of the surface of the patient's head, and to perform the calculations of the spatial distribution of the transducers modules relative to the patient anatomy. This information may be used with a 3D-printer to form a plastic support (frame) that fits snugly over the subject's head, like a custom helmet that has mounting holes for the insertion of the sub-arrays. The sub-arrays may have unique shapes, so they would fit only in the locations determined by the computer plan.

In the present example implementation, high-frequency transmit-receive elements are also integrated in the sub-array assemblies (e.g. 128 high-frequency elements), which can be used to determine the distance of the skull from the array. As noted above, such distances can be used to improve the registration of previously obtained volumetric imaging data to the array co-ordinates, and potential avoiding the need for additional intraoperative imaging. These high-frequency elements can be used continuously to track any head motion, and thus, there is no need for invasive pin fixation, as is the case with the current devices.

As described above with reference to FIG. 1, an elastic membrane may be provided that secures a liquid layer between the module surfaces and the membrane, thereby facilitating coupling to the skin when the patient-specific headset is worn.

It is expected that a headset fabricated according to the design described in the present example may be capable of driving 256 sub-arrays, resulting in an array of over 16,000 individual elements and 64 modules, although fewer elements may be required if adequate focusing can be achieved. The maximal area of human skull cap that can be used to propagate ultrasound is expected to vary approximately between 450 and 700 $cm^2$; thus, the complete array may not be fully populated, and may instead be sparse, which still maintains the high focus quality with the cost of increased power requirements. It is expected that such sparse array implementations will be compatible with all of the applications, which typically require low power during exposures (for example, such as opening of the blood-brain barrier and neuromodulation).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of fabricating a transcranial headset for diagnostic or therapeutic procedures, the method comprising:
   segmenting volumetric image data of a patient's head to obtain surface data characterizing an anatomical curvature of a portion of the patient's head;
   employing the surface data to generate a digital model of a patient-specific frame, such that the patient-specific frame conforms to the anatomical curvature of the portion of the patient's head;
   modifying the digital model such that the patient-specific frame comprises a plurality of transducer attachment interfaces for receiving and supporting a plurality of transducers in pre-selected positions and orientations relative to the patient's head;
   fabricating the patient-specific frame according to the digital model;
   securing the plurality of transducers to the transducer attachment interfaces; and
   generating transducer registration data characterizing the positions and orientations of the plurality of transducers relative to the volumetric image data.

2. The method according to claim 1 wherein fabricating the patient-specific frame comprises 3D printing the patient-specific frame.

3. The method according to claim 1 wherein fabricating the patient-specific frame comprises fabricating a mold and employing the mold to fabricate the patient-specific frame.

4. The method according to claim 1 wherein at least a portion of the transducers are phased-array ultrasound transducers, and wherein the pre-selected positions and orientations of the transducer attachment interfaces associated with the phased-array ultrasound transducers are selected to reduce grating lobes.

5. The method according to claim 1 wherein the plurality of transducers comprise one or more ultrasound transducers.

6. The method according to claim 1 wherein at least a portion of the plurality of transducers are phased-array transducers.

7. The method according to claim 6 wherein the phased-array transducers form a sparse array.

8. The method according to claim 6 wherein at least a portion of the phased-array transducers are magnetic resonance coils.

9. The method according to claim 1 wherein a first portion of the plurality of transducers are ultrasound transducers, and wherein a second portion of said plurality of transducers are optical transducers, such that the transcranial headset is suitable for performing photoacoustic detection.

10. The method according to claim 1 wherein a first portion of the plurality of transducers are ultrasound transducers, and wherein a second portion of the plurality of transducers are MRI coils, such that the transcranial headset is suitable for performing simultaneous ultrasound and MR imaging or sonications while using MR imaging.

11. The method according to claim 1 wherein a first portion of the plurality of transducers are MRI coils, and wherein a second portion of the plurality of transducers are positron emission detectors (PET), such that the transcranial headset is suitable for performing both MR and PET imaging.

12. The method according to claim 1 wherein a first portion of the plurality of transducers are MRI coils, and wherein a second portion of the plurality of transducers are positron emission detectors (PET), and third portion of the plurality of transducers are ultrasound transducer such that the transcranial headset is suitable for performing both MR and PET imaging while delivering ultrasound therapy or imaging.

13. The method according to claim 1 wherein at least a portion of the plurality of transducers are optical fibers operably connected to an optical coherence tomography system.

14. The method according to claim 1 further comprising connecting the plurality of transducers to control and processing hardware, the control and processing hardware being configured to employ the transducer registration data to control at least a portion of the plurality of transducers to focus energy at a pre-selected tissue region.

15. The method according to claim 1 wherein the patient-specific frame comprises a plastic support that conforms to the anatomical curvature of the portion of the patient's head.

16. The method according to claim 1 wherein each transducer attachment interface is configured to receive and support a transducer module comprising a sub-array of transducers.

17. The method according to claim 16 wherein each attachment interface and each transducer module have unique shapes, such that a given transducer module fits uniquely with its respective attachment interface.

18. The method according to claim 16 wherein each sub-array comprises transducer elements for forming a phased array.

19. The method according to claim 1 wherein the transcranial headset further comprises a coupling layer, wherein said coupling layer is provided adjacent to an inner surface of the patient-specific frame such that when the transcranial headset is worn, an outer surface of said coupling layer contacts distal surfaces of said plurality of transducers, and an inner surface of said coupling layer contacts the patient's head, thereby facilitating coupling of energy between the patient-specific frame and the patient's head.

20. The method according to claim 1 wherein the plurality of transducer attachment interfaces are configured such that the transducers are removable.

\* \* \* \* \*